United States Patent [19]

Weischedel

[11] Patent Number: 5,321,356
[45] Date of Patent: Jun. 14, 1994

[54] MAGNETIC INSPECTION DEVICE FOR ELONGATED OBJECTS AND INSPECTION METHOD

[75] Inventor: Herbert R. Weischedel, South Windsor, Conn.

[73] Assignee: NDT Technologies, Inc., South Windsor, Conn.

[21] Appl. No.: 888,587

[22] Filed: May 26, 1992

[51] Int. Cl.$^5$ ................. G01N 27/83; G01R 33/12
[52] U.S. Cl. .................................. 324/262; 324/240
[58] Field of Search ........ 324/227, 206, 213, 219–221, 324/232–235, 238–243, 260–262

[56] References Cited

U.S. PATENT DOCUMENTS

| | | | |
|---|---|---|---|
| 4,427,940 | 1/1984 | Hirama et al. | 324/240 |
| 4,546,316 | 10/1985 | Lang | 324/240 X |
| 4,659,991 | 4/1987 | Weischedel | 324/241 |
| 4,827,215 | 5/1989 | van der Walt | 324/232 X |

OTHER PUBLICATIONS

TRI Report 90328-D69, pp. 2,4 and 5, May 1989.
Development of a New Nondestructive Inspection System for Bridge Structures, Matzkin et al. (TRI), May 11–13, 1992.
Mechanische Grössen elektrisch messen, SPR=Seil-prüfgerät für Drahtseile bis 160 by Dr. Brandt GmbH and translation, (No Month) 1983.

Primary Examiner—Gerard R. Strecker
Assistant Examiner—Warren S. Edmonds
Attorney, Agent, or Firm—McCormick, Paulding & Huber

[57] ABSTRACT

A magnetic inspection device for non-destructively testing elongated objects such as large diameter wire cables is constructed with a number of flux carrying components that are assembled and disassembled in sections with a magnetic flux detector for detecting the loss of metallic cross-section and local discontinuities in the cable. The inspection device is moved bodily along a cable during the inspection process and in another embodiment the flux detector itself is the only component movable along the cable. Jack screws are utilized to mechanically separate or bring together the flux carrying components which are normally attracted to one another by powerful magnetic forces. Draw screws are also employed to pull together flux carrying components which are naturally repulsed from one another by the magnetic forces. Alignment pins are utilized to guide the components together in predetermined positional relationships during assembly processes.

30 Claims, 5 Drawing Sheets

MAGNETIC INSPECTION DEVICE FOR ELONGATED OBJECTS AND INSPECTION METHOD

BACKGROUND OF THE INVENTION

The present invention relates to a method and apparatus for non-destructively testing elongated objects such as wire rope or cable, rods, pipes and the like for loss of metallic cross-section and localized or distributed defects on the surface or within the object.

In my U.S. Pat. No. 4,659,991, I disclose a magnetic inspection device for testing elongated objects for loss of metallic cross-section, such as frayed cables, and local defects, such as individual broken wires forming the object. The device includes two pole pieces of opposite polarity for inducing magnetic flux in a section of the elongated object and a flux detector between the poles for detecting the changes of flux that arise due to the sought-for defects. The entire device is enclosed in a housing which is moved along the object to be tested or the object is pulled through the housing. Magnetic flux is induced into each portion of the elongated object, and the detector then senses flux changes to establish the presence or absence of the defect and the type of defect. The housing, the pole pieces and the detector are split into two at a hinge plane containing a hinge at one side of the housing for installing the inspection device on and removing the device from the object.

While the prior art device described above is satisfactory for measuring elongated objects up to a given size, there are still larger objects that cannot be handled by this prior art design with a single split housing. In particular, it has been learned that poor inspection results arise when there is insufficient magnetic saturation of the elongated object, and the larger the object, the more difficult it becomes to achieve saturation. For example, there are many suspension bridge cables and cables for mooring off shore drilling wells and exploration vessels that exceed 3½ (9 centimeters in diameter). Complete or nearly complete saturation of such cables, nonetheless, is required for testing. Magnetic testing of ferromagnetic cables without magnetic saturation or near-saturation leads to large inherent noise levels which correspondingly reduce the signal-to-noise ratios in the inspection equipment. Tests have clearly established that inspections at high saturation levels are far superior to those at low saturation levels.

Complete magnetic saturation of large steel cables is, however, quite difficult because it requires large, heavy magnets. At the present time both electromagnets and permanent magnets can be employed. Compared to permanent magnets, however, electromagnets are not desirable since they require a steel core and copper windings which makes them very heavy and bulky. In addition a high power current source is needed to energize the electromagnets. The high current sources lead to substantial dissipated energy which in turn requires heat sinking and even further weight increases. Therefore the size and weight of electromagnets are much greater than equivalent permanent magnets.

Permanent magnets, although they are lighter than equivalent electromagnets, cannot be turned on and off. Consequently, when employed in large quantity and in sizes needed to fully saturate large cables, the magnets create strong magnetic attraction and repulsion forces between the magnets, the various magnetic components and the cable, and such forces lead to significant handling difficulties. Between the weight of the magnetic assemblies and the magnetic forces, the use of permanent magnets, though far superior to electromagnets, can be impractical for large cables.

It is accordingly an object of the present invention to provide both a practical magnetic inspection device and method for magnetically inspecting elongated objects which can be used to non-destructively test large elongated objects for loss of metallic cross-section and local discontinuities.

SUMMARY OF THE INVENTION

The present invention resides in a magnetic inspection device and a method for non-destructively testing elongated objects for loss of metallic cross-section and local discontinuities. The device is used, for example, to inspect wire rope or cable, rods, pipes and similar elongated objects for defects that occur through use. For example, wire cables used for moorings and lifting cables may become abraded with use, and it is desirable to test such cables for the loss of metallic cross-section that occurs from such abrasion. Bridge suspension cables can also lose metallic cross-section due to corrosion. Other types of defects that arise in cables are local discontinuities that arise where only a few wires of the cable are broken either on the surface of the cable or internally. The inspection device of the present invention can be used to detect all of these types of defects.

The device which carries out the non-destructive testing method of the present invention has first and second flux carriers which include pole pieces for positioning at spaced stations along the object to be inspected. Magnetic means are coupled with the two pole pieces for inducing a magnetic flux through that section of the elongated object between the two pole pieces. The magnetic means are permanent magnets mounted within the pole pieces themselves, and the magnets are polarized to generate a forward flux path through the elongated object from one pole piece to the next.

A third flux carrier including a magnetic yoke interconnects the magnetic means and the first and second flux carriers for establishing a flux return path between the pole pieces externally of the elongated object. With such a construction a complete magnetic circuit extends along a forward path through the elongated object and a return path through the first, second and third flux carriers externally of the object.

Magnetic flux detection means having a flux sensor, such as a coil or Hall effect sensor, laterally adjacent the elongated object is provided for detecting flux changes in the magnetic circuit due to the loss of metallic cross-section or local discontinuities as the inspection device and the object are moved relative to one another. The changes in flux produce a signal in the sensor and that signal is then processed to identify more specifically the type of defect which causes the flux changes.

Mechanical separating means are operatively associated with at least one of the flux carriers for separating two flux carrying elements at a parting plane and thereby interrupting the magnetic circuit through the flux carriers. The mechanical separating means enables large, heavy magnets and associated pole pieces and yokes to be utilized for the purpose of generating magnetic fields that saturate the elongated objects during testing. Thus to alleviate the handling problem the device is divided into sections that are lighter and more manageable, and the mechanical separating means enables the sections to be separated more easily in opposition to the magnetic attraction forces that are established between the flux carrying elements. Accordingly, the inspection device and method can be carried out by a device that is broken down into smaller sections for both assembly and disassembly during testing operations.

Additionally, the separate flux carrying elements of the inspection device may be provided with alignment means so that during the assembly process the large magnetic attraction forces or repulsion forces do not interfere with the positioning of the components relative to one another in the assembled condition. For example, tapered alignment pins may be mounted in one of the elements and apertures mating with those pins may be provided in the other of the elements to bring the two elements into proper positional relationship as they are brought together.

The flux carriers may be sub-divided into a plurality of separable sections so that, for example, a plurality of magnets can be assembled in a single pole piece for saturating a large cable. To assemble such pole pieces drawing means are provided to pull the various pieces together in opposition to the repulsion forces that are generated when like poles are pulled together. Again alignment means may be employed to establish the correct positional relationship between the assembled elements.

One of the principal advantages of the present invention is that a large and powerful magnetic inspection device can be utilized with correspondingly large cables and other elongated objects. The device is subdivided into its various elements for both assembly and disassembly at the job site, and various means are provided to make the assembly and disassembly operations feasible in the environment of large magnetic fields and heavy magnetic components.

The invention also resides in a magnetic inspection device in which the magnetic flux detector means is movable back and forth between the pole pieces for detecting flux changes in those sections of the object that lie between the stations where the pole pieces are positioned. A device of this type is particularly useful for inspecting the main cables of suspension bridges which have permanently attached suspender cable bands that prohibit an inspection device from moving progressively along a cable from one end to the other during an inspection operation.

DESCRIPTION OF THE PREFERRED EMBODIMENTS

Figure 1:
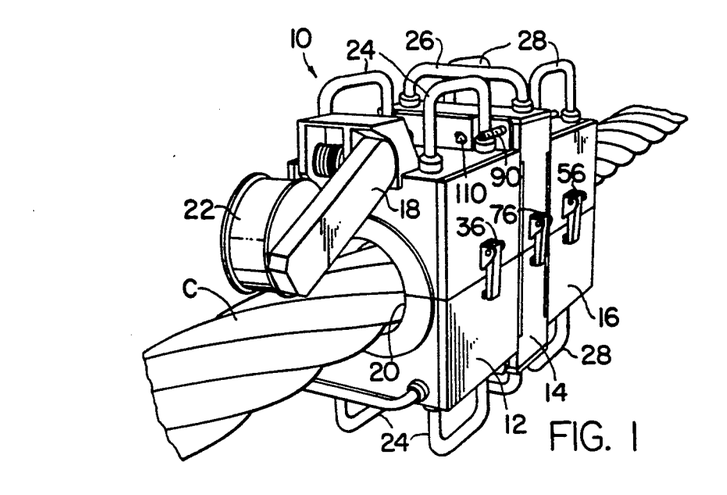
FIG. 1 is a perspective view of a magnetic inspection device according to the present invention on a wire cable during a testing operation.

FIG. 1 illustrates a magnetic inspection device, generally designated 10, for examining large diameter wire cable or rope, rods, pipes and the like. For example, the device may be employed for inspecting multi-strand wire cables C of up to 175 mm (7"). The device illustrated utilizes permanent magnets for magnetic saturation of the cable, and has a detection system that can be operated from a battery powered, notebook-type computer so that external power supplies are not needed. As shown in FIG. 1, the inspection device is mounted directly to the cable C and has three separate sections 12,14,16 which are interconnected and form a central passageway 20 through which the cable passes. A rotary encoder 22 is suspended on an arm 18 at the front of the device to measure the distance and speed at which the device travels along the cable C. For handling and pulling the inspection device 10, a plurality of handles 24 are connected with the section 12, a similar plurality of handles 28 with the section 16 and a pair of handles 26 with the section 14. A tow rope is connected to the handles at one end of the device for pulling the device along the cable, and a drag line is connected to the handles at the other end of the device. Between the tow rope and the drag line the precise position of the device along the cable can be controlled manually or by a winch system.

Figure 2:
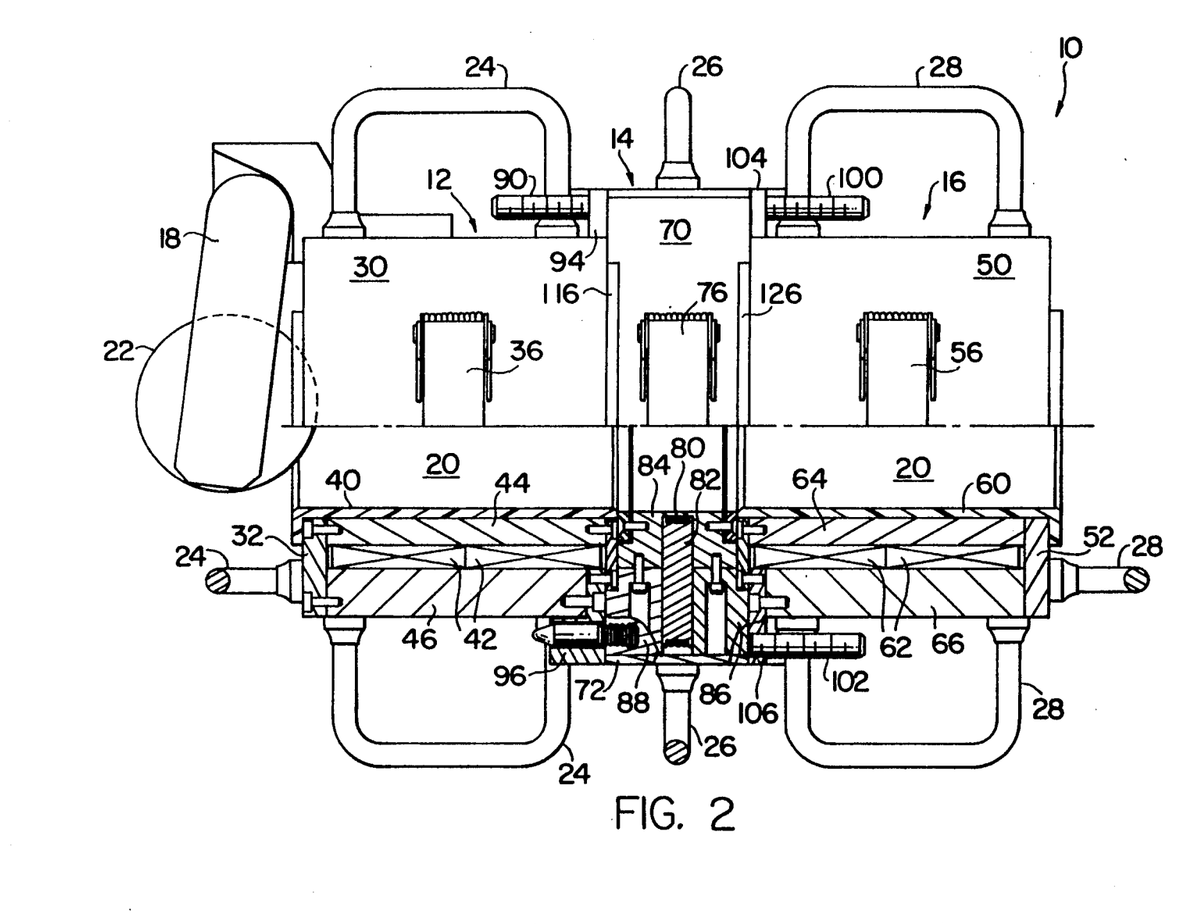
FIG. 2 is a partially sectioned side elevation view of the magnetic inspection device in FIG. 1.
Figure 3:
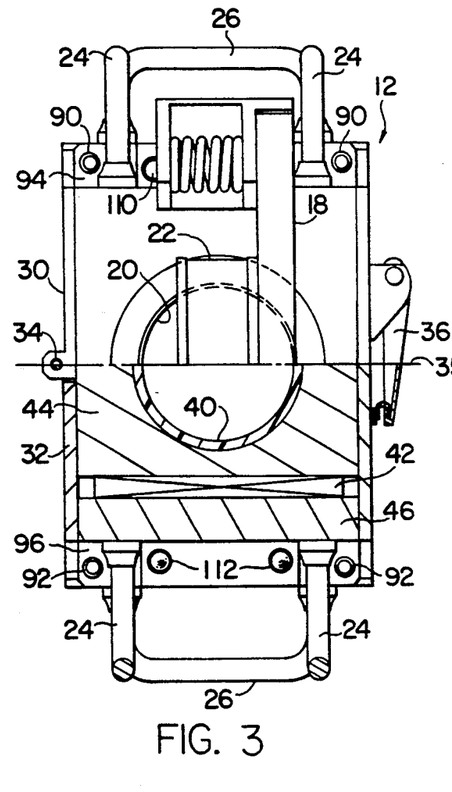
FIG. 3 is a partially sectioned end view of the magnetic inspection device in FIG. 1.
Figure 4:
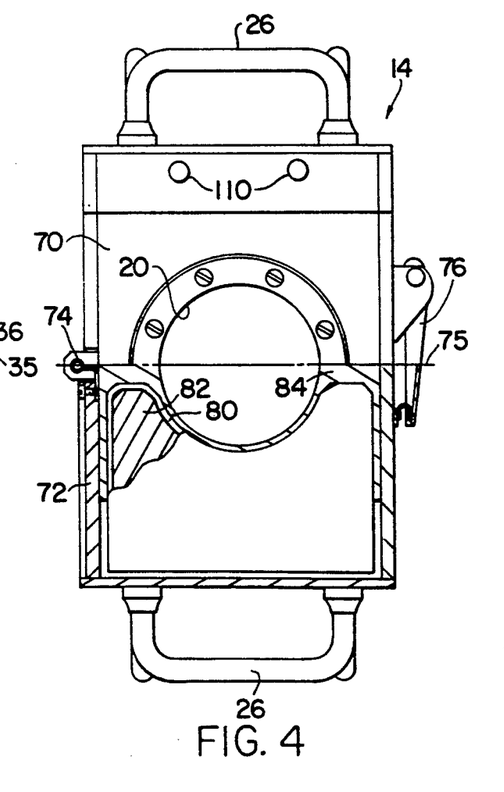
FIG. 4 is a partially sectioned end view of the magnetic flux detector section of the device.

FIGS. 2, 3 and 4 show the general construction and operation of the magnetic device 10 which can operate as disclosed more specifically in my U.S. Pat. No. 4,659,991.

The pole sections 12 and 16 contain pole pieces for inducing a magnetic field in the wire cable and have symmetrical constructions with respect to the central detector section 14 which contains the magnetic flux detector. The detector senses changes in the leakage flux due to loss of cross-sectional area in the cable or local discontinuities such as broken wires in the cable strands. As shown in FIG. 3 the pole section 12 (and correspondingly pole section 16) is split at a hinge plane 35 into an upper housing 30 and a lower housing 32 that are interconnected at one side by a hinge 34 and at the opposite side by a releasable draw latch 36. Thus the section 12 can be opened, placed around a cable and then closed with the draw latch 36 so that the cable is captured within the passageway 20. The passageway is lined with a plastic or soft friction bushing 40 so that the section slides smoothly along a cable.

A large magnet or set of magnets 42 is situated on a ferromagnetic pole piece 44 within the lower housing 32 for inducing a magnetic field in the cable within the passageway 20. One piece 46 of a ferromagnetic yoke is connected to the side of one or more magnets 42 opposite from the pole piece 44 and forms that portion of the housing 32 to which the handles 24 are connected. The upper housing 30 is symmetrically constructed with the same components including magnets and a yoke piece.

The pole section 16 has a construction symmetrical with that of the pole section 12 and includes hinged upper and lower housings 50,52, a draw latch 56, a friction bushing 60, magnets 62, a pole piece 64 and a ferromagnetic yoke piece 66.

The detector section 14, like the pole sections 12 and 16, is comprised by an upper housing 70 and a lower housing 72 that are interconnected by a hinge 74 and a draw latch 76 at opposite sides of the hinge plane 75. Within the lower housing 72 a magnetic flux detector composed primarily of a wire coil 80 wrapped on a ferromagnetic core piece 82 is mounted within a nonmagnetic material 84 and two ferromagnetic yoke pieces 86,88 that lie between the yoke pieces 46 and 66. The upper housing 70 is symmetrically constructed and includes similar wire coil and yoke pieces.

Like the pole sections 12 and 16, the detector section 14 containing the magnetic flux detector can be opened by releasing the draw latch 76 and swinging the two housings 70,72 about the hinge 74 to position the section on a cable to be inspected. The housings are then closed and the draw latch 76 secures the housings together. When the housings are closed, each coil 80 has one portion that lies in close proximity to the surface of the cable being inspected and senses changes in leakage flux at the cable surface due to local discontinuities and more general changes in metallic cross-section, all as described more fully in my U.S. Pat. No. 4,659,991 referenced above.

The magnet or magnets 42 in the pole section 12 are permanent magnets and are polarized in the radial direction with respect to the central passageway 20. Similarly, the magnet or magnets 62 in the pole section 16 are permanent magnets and are polarized in the radial direction but with a polarization which is opposite to the magnets 42. Thus magnetic flux is induced through the pole pieces 44,64 into a section of cable lying within the passageway 20 and a magnetic flux path or circuit extends from one pole piece to the other through the section of cable.

The yoke sections 46,66,86,88 together with the coil cores 82 establish a flux path externally of the cable between the magnets 42,62 and, thus, a complete magnetic circuit consisting of a forward flux path through the cable and a return flux path through the yoke pieces is formed. That circuit, of course, is replicated in parallel in the upper housings in which the magnets have the same radial polarizations and add to the magnetic flux through the cable.

Ideally the magnets are rare earth type magnets with sufficient strength to saturate the section of cable within the device 10 so that leakage flux and changes in leakage flux at the surface of the cable can be detected. With cables of large diameter large magnets, pole pieces and yoke pieces are required. The size and weight of such components make the device quite heavy and difficult to manipulate both onto the cable and off of the cable. Correspondingly, with permanent magnets the retraction and repulsion forces as explained in more detail below are quite large and contribute to the difficulty of manipulating the magnetic inspection device. In spite of these difficulties, the magnetic inspection device designed in accordance with the present invention overcomes these difficulties and provides a device which can be used with large diameter elongated objects to produce clear detection signals with a high signal-to-noise ratio.

In accordance with one aspect of the present invention the components within the magnetic circuit formed by the components in the inspection device 10 are divided longitudinally into the series of modules or sections 12,14,16 that are of reduced weight and size and can therefore be serially mounted or removed from the cable C by one or two workmen. In addition, mechanical separating means are provided between the various magnetic elements to separate those elements in opposition to the powerful magnetic attraction forces that are created when the sections are assembled. When the elements are separated, the mutual attraction forces are greatly diminished.

Figure 5:
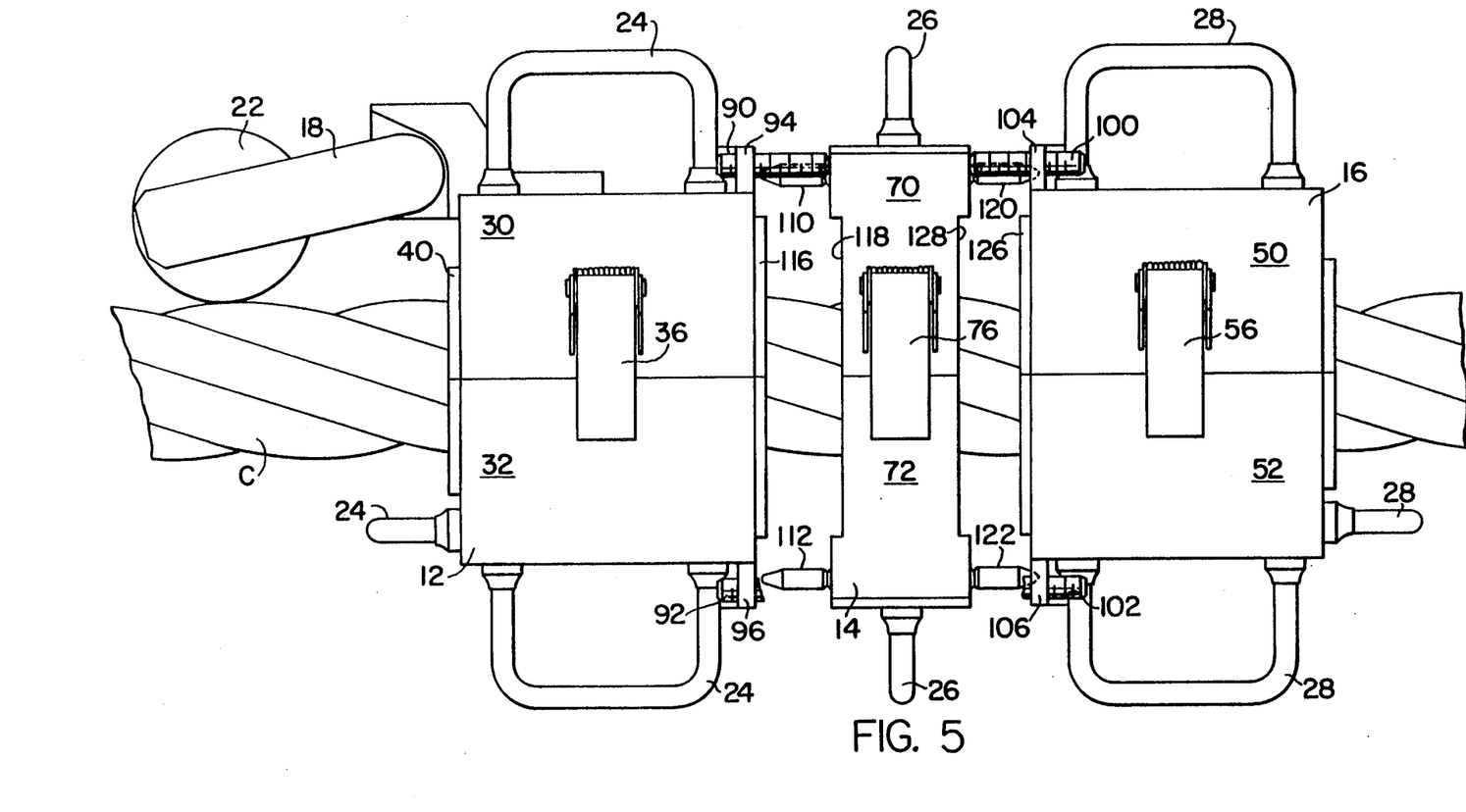
FIG. 5 is a side elevation view showing the magnetic inspection device with the sections separated from one another for assembly or disassembly on a wire cable.

FIG. 5 shows the pole sections 12 and 16 separated from the detector section 14 to which the sections 12 and 16 are normally attracted. When the sections are separated, the yoke pieces 46 and 66 are naturally separated from the pieces 86,88 and the magnets 42,62 are also separated. Since the magnetic attraction forces decrease drastically with increases in the distance between the magnets and flux carrying elements, a slight separation of the sections as shown interrupts the magnetic circuit and effectively reduces the attraction forces so that the sections can be manually separated by grasping the handles 24,26,28.

Figure 6:
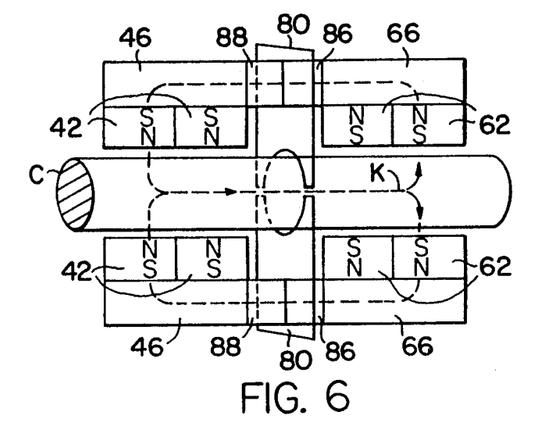
FIG. 6 is a schematic diagram of the magnetic inspection device in the assembled form.
Figure 7:
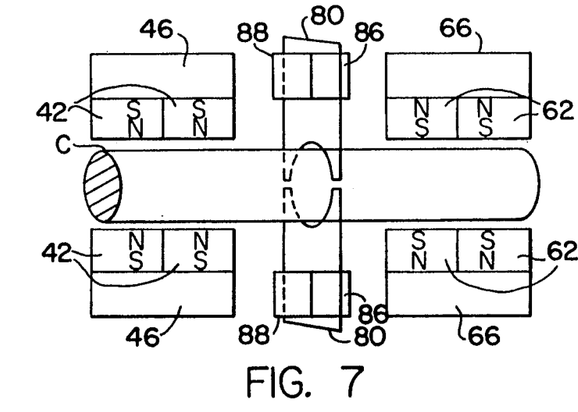
FIG. 7 is a schematic diagram of the magnetic inspection device in a separated form.

The breakdown or interruption of the magnetic flux paths through the separated components is illustrated schematically in FIGS. 6 and 7. In FIG. 6 the components are assembled in adjacent relationship. The magnets 42 on one side of the detection coil 80 have a polarity which is the reverse of the polarity of the magnets 62 on the opposite side of the coil. Thus there is a powerful attraction force between the yoke pieces 46 and 66 as well as directly between the magnets themselves. It is this magnetic polarity which establishes the flux circuit K through the section of the cable C between the pole pieces.

FIG. 7 in contrast illustrates schematically the positional relationship of the components along the cable C when the sections have been separated as shown in FIG. 5. It will be observed that the magnetic circuit K is effectively interrupted due to the spacing of the magnets 42,62 and yoke pieces 46,86,88,66 along the cable. At the same time the magnetic attraction forces are substantially dissipated so that the sections can be further separated and then split open for removal from the cable.

The mechanical separating means in the embodiment of the invention illustrated in FIGS. 1-7 includes a plurality of jack screws 90,92 shown in FIGS. 2, 3 and 5, mounted respectively in flanges 94,96 on the pole section 12 and a similar plurality of screws 100,102 mounted in flanges 104,106 on the pole section 16. For purposes of illustration, the jack screws in the lower portion of the sections 12 and 16 are broken away. Each of the jack screws operates against a reaction pad or surface on the detector section 14 so that advancing the jack screws toward the section 14 causes the sections to separate from one another in opposition to the mutual magnetic attraction forces as shown in FIG. 5. Since the screws provide a mechanical advantage substantially greater than one, generally 20:1 or more, sufficient forces can be generated to separate the sections by an amount sufficient to dissipate the magnetic forces and allow the sections to be manually pulled apart for disassembling the magnetic inspection device.

Once the sections 12, 14 and 16 have been separated by the jack screws and further manual displacement by workmen, the draw latches 36,56,76 are released and each section is split open by pivoting the sections about their respective hinges 34,74. It will be observed from FIGS. 6 and 7 that the magnets 42,62 in the respective housings of the pole sections tend to repel each other and the draw latches are provided to assist in pulling the housings together. By the same token, the process of splitting or opening the housings by pivoting the upper and lower housings about the hinges is not complicated by magnetic forces and in fact repulsion forces between the two housings aid in the process.

The process of assembling the magnetic inspection device 10 on a cable to be inspected is also facilitated by the sectioned design, and is accomplished essentially by performing the steps of disassembly in reverse order. First the individual sections are split open and mounted in spaced relationship along the cable to be tested so that the sections are not drawn together by the magnetic attraction forces. The draw latches 36,56,76 are used to pull the respective housings 30,32, 70,72, 50,52 of each section together with the cable C residing in the central passageway 20 through each section.

The jack screws 90,92 and 100,102 are initially extended longitudinally from the pole sections 12,16 toward the detector section 14. One of the pole sections 12 or 16 is moved manually toward the detector section 14 until the jack screws make contact with the reaction pad on the detector section. The pole section is also oriented properly about the cable with respect to the detector section, and then the jack screws are backed away from the detector section generally by equal increments to allow the two sections to come together.

Alignment pins 110 at the top of the detector section 14 are positioned to register with a corresponding set of apertures in the flange 94 of the section 12, and similar pins 112 at the bottom of the section 14 register respectively with alignment holes in the flange 96 at the bottom of the section 14. As illustrated the alignment pins 110,112 have a tapered or bullet nose to insure that the two sections are guided together in proper positional relationship as the jack screws are withdrawn. When the sections 12 and 14 are properly guided together by the pins, a face plate 116 on the section 12 is received in a corresponding recess 118 of the detector section 14.

The pole section 16 is mounted on the cable C and joined with the detector section 14 in the same manner as the pole section 12 through the use of the jack screws 100,102 and bullet-nosed guide pins 120,122 which mate with apertures in the flanges 104,106 in a manner corresponding to the guide pins 110,112. When the sections 14 and 16 are in proper positional relationship, a face plate 126 on the section 116 mates with a corresponding recess 128 on the detector section 14 as shown in FIG. 2.

Accordingly, the modular or sectionalized construction of the magnetic inspection device 10 allows the inspection device to be readily assembled or disassembled by several men on a large cable for performing an inspection operation. Although the device is divided into a series of axially separable sections for longitudinal assembly on a cable, the construction offers the advantage that the assembly process can be carried out by a small number of workmen and yet large powerful magnetic fields can be generated by the assembled device so that the magnetic inspection process can be carried out on large cables at saturation or near-saturation conditions.

Figure 8:
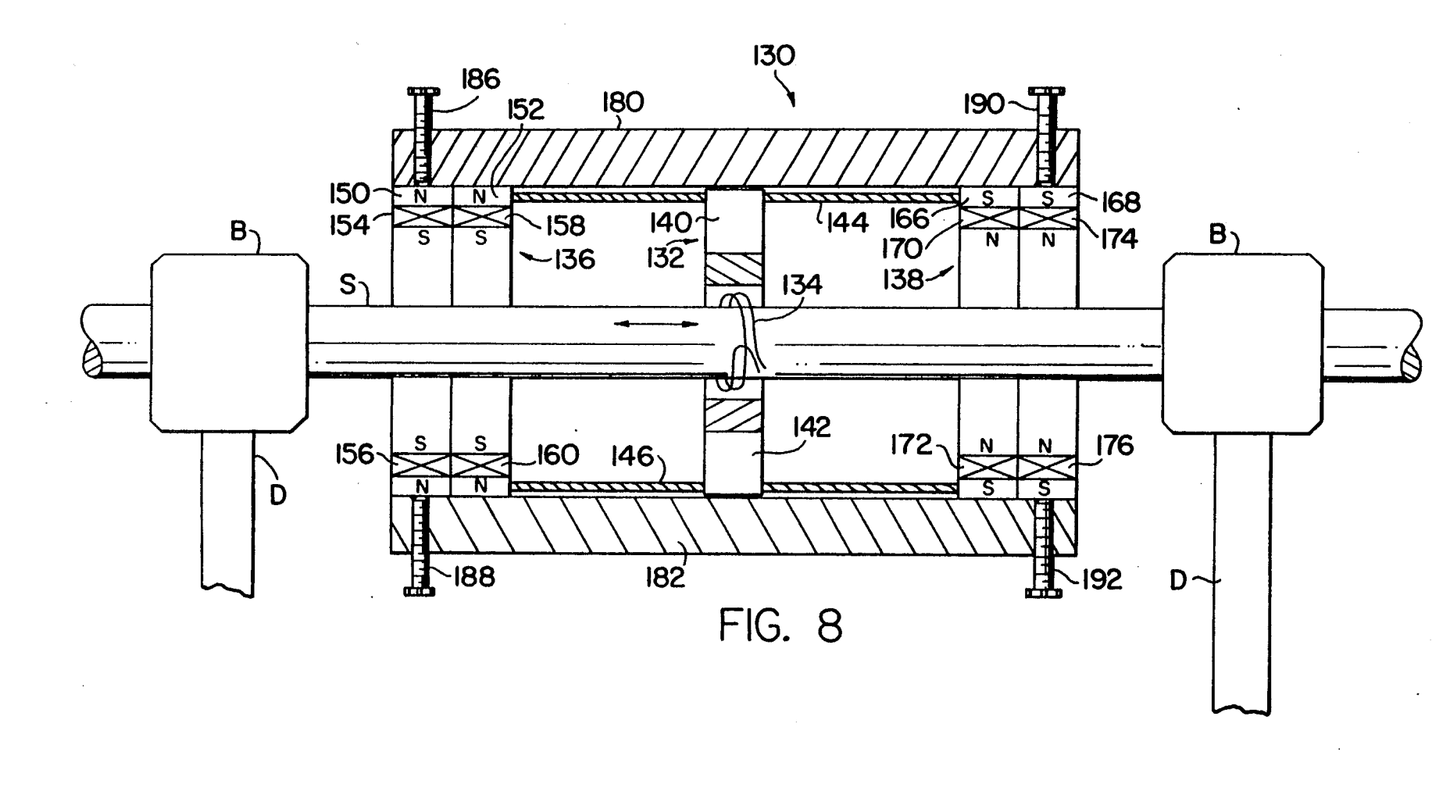
FIG. 8 is a schematic elevation view in section and shows an alternate embodiment of the magnetic inspection device.
Figure 9:
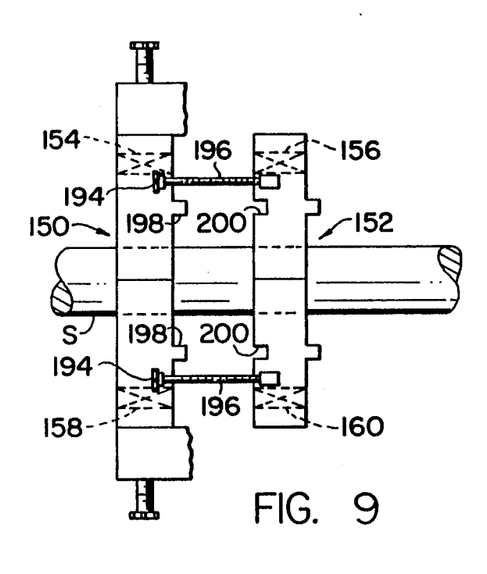
FIG. 9 is a schematic view of the pole pieces in the inspection device of FIG. 8.

FIGS. 8 and 9 illustrate another embodiment of the magnetic inspection device which may utilize the modular or sectionalized construction and which is particularly useful for inspecting the main cables S of suspension bridges. As shown in FIG. 8 such cables frequently include a suspender cable band B at periodic intervals along the cable for securing the suspender cables D. The suspender cables extend downwardly and are connected with the bridge deck. The bands B interfere with the type of inspection device 10 illustrated in FIGS. 1-7 since they prohibit the device from being advanced progressively along the cable during the inspection process. Accordingly, the magnetic inspection device 130 is designed with a detector section 132 including a detection coil 134 which is movable back and forth relative to the pole pieces 136,138 at opposite ends of the device to inspect the section of cable between the pole pieces. For this purpose the detector section 132 is provided with two drive motors 140,142 mounted on the section 132 and mechanically coupled respectively with lead screws 144,146. In this embodiment the lead screws are fixed at each end in the pole pieces 136,138 so the drive motors can pull the detector section 132 back and forth between the pole pieces. Alternatively, however, the lead screws 144,146 may be threadibly engaged with the detector section 132 and the drive motors may be mounted on the pole pieces for rotating the lead screws and pulling the detector section back and forth between the pole pieces.

Functionally the device 130 operates in the same manner as the inspection device 10 by generating a saturating magnetic field within the section of the cable under inspection and detecting loss of metallic cross-section or local discontinuities through the changes in magnetic flux at the surface of the cable.

For comparable cable capacities, the magnetic inspection device 130 is likely to be much larger and heavier than the magnetic inspection device 10 and, accordingly, the modular or sectionalized construction is also used for the device 130.

In particular the pole piece 136 is sub-divided at a parting plane into two annular, side-by-side sub-sections 150,152 that are split into upper and lower housings at a hinge plane for mounting on the cable in the same manner as the pole sections in the inspection device 10. The subsection 150 contains a permanent magnet 154 in the upper housing and a permanent magnet 156 in the lower housing. The magnets 154 and 156 have opposed radial polarizations as do the magnets 158,160 in the adjacent subsection 152.

The pole piece 138 at the opposite end of the inspection device 130 has essentially the same construction with subsections 166,168 each containing radially polarized magnets 170,172,174,176 respectively. The magnets in the pole piece 138, however, have a polarization opposite to the magnets in the pole piece 136 so that a magnetic field is induced into the section of the cable between the pole pieces at saturation or near saturation levels.

A flux return path between the pole pieces 136 and 138 is established by an upper yoke 180 and a lower yoke 182. The yokes are both constructed of a ferromagnetic material and complete the magnetic circuit externally of the cable S.

For assembling and disassembling the magnetic inspection device 130 with the modular construction, mechanical separating means are provided on the yokes in the form of jack screws 186,188,190,192. The jack screws operate against reaction pads or surfaces on the pole pieces 136,138 in order to separate the yokes from the pole pieces and interrupt the magnetic circuit. Once the circuit has been interrupted, the magnetic attraction forces are minimized and the yoke pieces can be removed entirely from the mounted device.

After the yokes have been removed, the pole pieces 136,138 are disassembled. It will be noted that the magnets within the side-by-side subsections 150,152 of the pole piece 136 have like polarizations and, consequentially, mutual magnetic repulsion forces must be overcome during both disassembly and assembly operations. As shown in FIG. 9, the subsection 150 is provided with a plurality of eyelets 194, and the subsection 152 is provided with a corresponding plurality of draw screws 196. If there are more than two side-by-side subsections, the same construction and sets of draw screws would be provided between adjacent subsections.

During disassembly, the draw screws are loosened incrementally in substantially equal amounts and the repulsion forces cause the, subsections 150,152 to separate longitudinally as shown in FIG. 9. As the distance between the subsections increases, the mutual repulsion forces diminish rapidly until the subsections can be handled manually and the draw screws are removed from the subsections. The subsections are then split and removed individually from the cable S. The pole piece 138 is disassembled in the same fashion.

The assembly process for the inspection device 130 is accomplished by reversing the order of the steps in the disassembly process. The subsections 150,152 are assembled on the cable S at longitudinally spaced stations and the draw screws 196 are utilized to pull the sections together in opposition to the repulsion forces of the magnets. Alignment means in the form of tapered guide pins 198 and corresponding recesses 200 assist in guiding the sections together in a pre-established positional relationship. The pole piece 138 is assembled in the same fashion.

Once the pole pieces have been assembled, the yokes 180 and 182 are joined to the pole pieces with the aid of the jack screws. Alignment means may also be provided between the yokes and the pole pieces.

Accordingly the magnet inspection device 130 can be readily assembled and disassembled by several workmen in spite of the weight of the device and the powerful magnetic attraction and repulsion forces that exist between the magnetic components of the device. The device is modular and allows additional subsections to be added to each of the pole pieces in order to develop magnetic flux in the cable at saturation or near-saturation conditions. The device can be assembled to straddle one or more bands B along the cable S which permits the detector section 132 to be moved directly adjacent the bands to inspect the entire length of the cable between the bands. The bands are likely to produce some distortion of the magnetic field which must be accounted for in measuring the output signals from the coil 134. Since the detector section 132 can normally be positioned at a sufficient distance from each of the pole pieces 136,138, disassembly of the detector section does not involve any significant difficulty from the magnetic forces.

While the present invention has been described in several preferred embodiments, numerous modifications and substitutions can be made without departing from the spirit of the invention. For example, the mechanical separating means is illustrated in each embodiment as a jack; however, equivalent levers, cams, hydraulic pistons, wedges and similar high force generating devices whose mechanical displacements can be readily controlled may be substituted. The alignment means illustrated consist of guide pins and corresponding holes; however, equivalent tapered housings, guide rods and tapered channels may be employed with equally satisfactory results.

The flux detector or sensor described in the embodiment of the device is a simple coil but other types of flux sensors such as Hall-effect sensors may be used with equivalent results. The invention permits longitudinal assembly operations to be carried out by subdividing the heavy and magnetically powerful elements of the device into a series of sections and distributing those sections at spaced stations along the cable. The assembly and disassembly process can be carried out with any number of sections needed for magnetic saturation. Accordingly, the present invention has been described in several preferred embodiments by way of illustration rather than limitation.

I claim:

1. A magnetic inspection device for non-destructively testing loss of metallic cross-section and local discontinuities in elongated objects such as wire cable, and the like comprising:
   a first flux carrier including a magnetic pole piece for positioning adjacent the elongated object to be inspected;
   a second flux carrier including a magnetic pole piece for positioning adjacent the elongated object in spaced relationship from the pole piece of the first flux carrier;
   magnetic means for inducing magnetic flux through the two pole pieces of the first and second flux carriers along a forward flux path in a section of the elongated object extending between the two pole pieces;
   a third flux carrier including a magnetic yoke interconnecting the magnetic means and the first and second flux carriers for establishing a magnetic flux return path between the magnetic pole pieces externally of the elongated object whereby a complete magnetic circuit includes the forward flux path in the elongated object and the return path in the first, second and third flux carriers;
   magnetic flux detector means having a flux sensor laterally adjacent the elongated object for detecting flux changes in the magnetic circuit due to loss of metallic cross-section or local discontinuities; and
   mechanical separating means operatively associated with at least one of the flux carriers for separating two flux-carrying elements of the carriers at a parting plane, from an otherwise assembled condition interrupting the magnetic circuit through the flux carriers and reducing the magnetic attraction forces of the flux carriers.

2. A magnetic inspection device as defined in claim 1 wherein the mechanical separating means includes a force generator and reacting means wherein the reaction therebetween creates a mechanical advantage greater than one.

3. A magnetic inspection device as defined in claim 2 wherein the force generator comprises a jack screw mounted on one of the two flux carrying elements and operable against a seat on the other of the two flux carrying elements.

4. A magnetic inspection device as defined in claim 1 wherein:
   the device including the first, second and third flux carriers is divided longitudinally into a plurality of adjacent sections with parting planes between each section; and the mechanical separating means is connected to one of the sections and operates against the adjacent section to separate the sections and interrupt the magnetic circuit.

5. A magnetic inspection device as defined in claim 1 wherein:

the magnetic yoke of the third flux carrier connects with the first flux carrier at the parting plane; and the mechanical separating means is connected to one of the first and third flux carriers and operates against the other of the first and third flux carriers to separate the yoke and interrupt the magnetic circuit between the two flux carriers.

6. A magnetic inspection device as defined in claim 1 wherein:

the first flux carrier and the second flux carrier are disposed on opposite sides of the magnetic flux detector means for series arrangement along an elongated object, the first flux carrier and the second flux carrier each being separable from the magnetic flux detection means at associated parting planes; and the mechanical separating means is operatively associated with one of the first and second flux carriers for separating said one of the flux carriers from the flux detector means at the parting plane associated with the detection means and said one of the flux carriers.

7. A magnetic inspection device as defined in claim 6 further including alignment means associated with the flux detector means and said one of the flux carriers for guiding the detector means and said one of the flux carriers into a predetermined position with respect to one another.

8. A magnetic inspection device as defined in claim 6 wherein the guide means comprises tapered alignment pins.

9. A magnetic inspection device as defined in claim 6 wherein:

said one of the flux carriers is sub-divided into a plurality of separable sections for series arrangement along an elongated object;

the magnetic means for inducing magnetic flux are mounted in at least two of the separable sections of said one of the flux carriers; and alignment means are provided for guiding two of the separable sections into predetermined positional relationship.

10. A magnetic inspection device as defined in claim 6 wherein:

said one of the flux carriers is sub-divided into a plurality of separable sections for series arrangement along an elongated object;

the magnetic means for inducing magnetic flux are mounted in at least two of the separable sections of said one of the flux carriers; and drawing means are connected with the two separable sections of said one of the flux carriers for pulling the two sections together in opposition to magnetic repulsion of the sections.

11. A magnetic inspection device as defined in claim 10 further including alignment means provided on the two sections of said one of the flux carriers for guiding the two sections into a predetermined positional relationship as the drawing means pulls the two sections together.

12. A magnetic inspection device for nondestructively testing elongated objects comprising:

a first section defining a pole piece and including a magnet for inducing a magnetic field in an elongated object at a first longitudinal station along the object;

a second section defining a pole piece and including a magnet for inducing a magnetic field in the elongated object at a second longitudinal station displaced along the object from the first station;

the magnets in the first and second sections being positioned and poled to generate magnetic fields which establish a magnetic circuit extending from one section to the other through the elongated object;

a third section interposed between the first and second sections, and containing a magnetic flux detector for detecting magnetic flux in the magnetic circuit established by the magnets;

a ferromagnetic yoke extending between the first and second sections and defining a flux path completing the magnetic circuit externally of the elongated objects; and mechanical separating means coupled with flux carrying portions of the yoke and at least one of the first and second sections in the magnetic circuit for parting the flux carrying portions from an otherwise assembled condition in opposition to the magnetic attraction forces and interrupting the magnetic circuit to disassemble the inspection device.

13. A magnetic inspection device as defined in claim 12 wherein:

the first, second and third sections are separable from each other at parting planes; and the mechanical separating means are coupled with each of the sections for separating the sections at the parting planes.

14. A magnetic inspection device as defined in claim 13 wherein the yoke extends through each of the sections and is divided in parts at the parting planes between the sections.

15. A magnetic inspection device as defined in claim 12 wherein:

the yoke extends between the first section defining a pole piece and the second section defining a pole piece; and the mechanical separating means is connected with the yoke and the first section for separating the yoke from the first section and interrupting the flux path and magnetic circuit through the yoke.

16. A magnetic inspection device as defined in claim 12 wherein:

the mechanical separating means includes a jack screw.

17. A magnetic inspection device as defined in claim 12 further including alignment means connected with the first, second and third sections for bringing the sections together in a predetermined positional relationship.

18. A magnetic inspection device as defined in claim 17 wherein the alignment means includes a plurality of alignment pins extending generally parallel to the elongated object.

19. A magnetic inspection device as defined in claim 12 wherein the first section defining a pole piece has a central passageway through which the elongated object passes during testing, the section is divided into two housings at a plane in which the axis of the passageway lies, and the two housings are connected together by a hinge for mounting the section on an elongated object.

20. A magnetic inspection device as defined in claim 19 wherein:
pole pieces and magnets are mounted in each half of the first section in opposing relationship whereby magnetic repulsion forces are created between the two housing; and
a draw latch is provided for pulling and securing the two hinged housings of the section together about an elongated object.

21. A magnetic inspection device as defined in claim 12 further including:
a fourth section defining a pole piece and including a further magnet for inducing a magnetic field in the elongated object adjacent to and in parallel with the first section whereby the magnet in the fourth section and the magnet in the first section cause mutual repulsion forces between the first and fourth sections; and
drawing means connected with the first and fourth sections for pulling the two sections together.

22. A magnetic inspection device as defined in claim 21 further including alignment means for bringing the first and fourth sections into a predetermined positional relationship when the drawing means pulls the sections together.

23. A magnetic inspection device as defined in claim 12 wherein:
the first and second sections are mounted in spaced apart relationship, and the third section is mounted in the space between the first and second sections for movement toward and away from the first and second sections.

24. A magnetic inspection device for testing elongated objects comprising:
a first pole piece having a magnet for inducing magnetic flux in an elongated object at one station;
a second pole piece having a magnet for inducing flux in an elongated object at a second station,
the first and second pole pieces being of opposite magnetic polarity whereby the induced magnetic flux extends through the elongated object between the first and second stations;
means for holding the first and second pole pieces in spaced relationship at the first and second stations;
a yoke extending between the first and second pole pieces and providing a flux return path for completing the magnetic circuit between the first and second pole pieces; and
magnetic flux detector means movable back and forth between the first and second pole pieces for detecting flux changes in the elongated object between the first and second stations.

25. A magnetic inspection device as defined in claim 24 wherein:
the first pole piece is constructed from a plurality of side-by-side pole sections separable at parting planes generally perpendicular to an elongated object extending between the first and section stations, each section having a magnet and being similarly polarized whereby the mutual repulsion forces are reacted between the sections; and
drawing means are provided for pulling the plurality of pole sections into side-by-side relationship.

26. A magnetic inspection device as defined in claim 24 wherein:
alignment means are further provided for guiding the plurality of pole sections into side-by-side relationship and a predetermined positional relationship.

27. A magnetic inspection device as defined in claim 24 wherein:
the first pole piece is constructed from a plurality of side-by-side pole sections separable at parting planes generally perpendicular to an elongated object extending between the first and section stations, each section having a magnet and being similarly polarized whereby the mutual repulsion forces are reacted between the sections; and
alignment means are further provided for guiding the plurality of pole sections into side-by-side relationship and a predetermined positional relationship.

28. A method for magnetically inspecting elongated objects by inducing magnetic flux in the object through a first pole piece at one station along the object and a second pole piece at a second station along the object, the two pole pieces being magnetically interconnected by means of a yoke whereby a forward flux path is established through the elongated object between the first and second stations and a return flux path is established through the yoke, and detecting the changes in flux by means of a flux detector positioned between the first and second pole pieces, the method comprising:
dividing the pole pieces and magnetic flux detector into separate sections;
positioning the separate sections along an elongated object in spaced relationship;
moving the sections relative to one another along the elongated object in order to assemble the sections for a test;
conducting a test with the assembled sections; and
disassembling the sections by separating the sections and positioning them at longitudinally spaced stations along the elongated object and then
removing the sections individually from the elongated object.

29. A method for magnetically inspecting elongated objects as defined in claim 28 wherein the step of removing includes slitting each section in half along a plane containing the central axis of the object.

30. A method for magnetically inspecting elongated objects as defined in claim 28 wherein;
each of the pole pieces is divided into a plurality of subsections having parting planes extending perpendicular to the elongated object; and
the step of disassembling further includes the step of separating the subsections of the pole pieces along the elongated object and then removing the subsections from the object.

* * * * *